US012599503B2

(12) United States Patent
Jaschke et al.

(10) Patent No.: US 12,599,503 B2
(45) Date of Patent: Apr. 14, 2026

(54) GOGGLE LENS

(71) Applicant: UVEX ARBEITSSCHUTZ GMBH,
Fürth (DE)

(72) Inventors: Simon Jaschke, Burgthann (DE);
Marco Wacker, Wilhermsdorf (DE);
Florian Kühnlein, Veitsbronn (DE);
Martin Wolf, Ansbach (DE)

(73) Assignee: UVEX ARBEITSSCHUTZ GMBH,
Fürth (DE)

( * ) Notice: Subject to any disclaimer, the term of this
patent is extended or adjusted under 35
U.S.C. 154(b) by 309 days.

(21) Appl. No.: 18/264,092

(22) PCT Filed: Jan. 21, 2022

(86) PCT No.: PCT/EP2022/051308
§ 371 (c)(1),
(2) Date: Aug. 3, 2023

(87) PCT Pub. No.: WO2022/171415
PCT Pub. Date: Aug. 18, 2022

(65) Prior Publication Data
US 2024/0082062 A1 Mar. 14, 2024

(30) Foreign Application Priority Data
Feb. 9, 2021 (DE) .................... 10 2021 201 180.2

(51) Int. Cl.
*A61F 9/02* (2006.01)
(52) U.S. Cl.
CPC .................................. *A61F 9/029* (2013.01)

(58) Field of Classification Search
CPC . A61F 9/029; A61F 9/06; G02C 11/08; A42B
3/245; B63C 11/12; H05B 1/023; H05B
3/0004; H05B 3/84; H05B 2203/005;
H05B 2203/011; H05B 2203/013; H05B
2203/037; H05B 2214/04
See application file for complete search history.

(56) References Cited

U.S. PATENT DOCUMENTS

| | | | |
|---|---|---|---|
| 11,994,750 B2 * | 5/2024 | Berg ......................... A42B 3/22 |
| 2010/0126345 A1 | 5/2010 | Gupta |
| 2011/0126345 A1 | 6/2011 | Matsumoto |
| 2013/0212765 A1 | 8/2013 | Cornelius et al. |
| 2014/0317836 A1 * | 10/2014 | McCulloch ............. A61F 9/029 |
| | | | 2/435 |
| 2018/0000648 A1 | 1/2018 | McCulloch et al. |
| 2018/0014359 A1 | 1/2018 | Simonato et al. |

(Continued)

FOREIGN PATENT DOCUMENTS

| | | |
|---|---|---|
| DE | 1951643 A | 12/1966 |
| DE | 2718679 A1 | 11/1978 |
| DE | 202009010212 U1 | 1/2010 |

(Continued)

*Primary Examiner* — Nelson M Rosario
(74) *Attorney, Agent, or Firm* — FisherBroyles, LLP;
Roger L. Browdy; Ronni S. Jillions

(57) ABSTRACT
A goggle lens comprises a main body and at least one
transparent, electrically conductive coating that covers the
main body at least partly, as well as electrical contact means
which cover the at least one coating partly and are in
electrical connection with the at least one coating and also
form at least one electrical heating zone.

8 Claims, 12 Drawing Sheets

(56)                References Cited

U.S. PATENT DOCUMENTS

2018/0124878 A1      5/2018  Fritz et al.
2020/0409183 A1*  12/2020  Saylor ..................... G02C 7/12

FOREIGN PATENT DOCUMENTS

DE      102015114507  A1    3/2017
EP              1072205  A2    1/2001
EP              1072205  A3    2/2001
EP              3709775  A1    9/2020
WO      2015048564  A1    4/2015
WO      2017070628  A1    4/2017

* cited by examiner

GOGGLE LENS

CROSS-REFERENCES TO RELATED APPLICATIONS

This application claims the priority of German Patent Application, Serial No. DE 10 2021 201 180.2, filed Feb. 2, 2021, the content of which is incorporated herein by reference in its entirety as if fully set forth herein.

FIELD OF THE INVENTION

The invention relates to a goggle lens comprising a main body, comprising at least one transparent, electrically conductive coating which covers the main body at least partly, comprising electrical contact means which partly cover the at least one coating, are in electrical connection with the at least one coating and partly form at least two electrical heating zones which are openable independently of each other; and comprising electrical conductor paths which are electrically connected to the contact means for energizing the contact means. Furthermore, the invention is directed to a pair of goggles having at least one lens. The goggles are particularly designed as safety goggles or winter sports goggles, such as ski goggles, snowboard goggles or the like.

BACKGROUND OF THE INVENTION

Heatable goggle lenses are generally known from the prior art. These often have an extremely high energy consumption during operation, which re-quires frequent charging or replacement of batteries. Goggles having such lenses are usually bulky and heavy due to the circuits or printed circuit boards used. WO 2015/048564 A1 discloses generic anti-fog eye shields, which can be used, for example, in goggles or for eye protection. The eye shield comprises a conductive heating element which is divided into a plurality of regions, for example, to allow individual heating of the regions. A plurality of electrically conductive regions of optically transparent, electrically resistive, conductive heating material is disposed on a substrate. The eye shield further comprises at least two bus bars which are connected to the conductive regions and are configured to connect the conductive regions to the power source. According to FIG. 2, three electrically insulated heating element regions are arranged on the eye shield, which are connected to a power source. Segmenting a heating element into multiple regions allows the option of heating each region separately, such as with separate batteries or with PWM channel controls. Heating of these anti-fog eye shields is not always satisfactory.

US 2011/0126345 A1 discloses a fog-resistant structure, such as lenses for eye protection. A transparent conductive film is formed on one surface of the disc. A first linear electrode is provided at the top of the surface of the disc and a second linear electrode is provided at the bottom of the surface of the disc. The ends of the electrodes are connected to a power source. Each end of an electrode is configured as a connection terminal. The transparent conductive film may be divided into at least left, right, top and bottom sections. The electrodes are then connected to the corresponding sections.

DE 10 2015 114 507 A1 discloses an electrically heatable laminar body, the first carrier of which is covered on one or both sides with non-transparent conductor paths. Highly bundled conductor paths, such as contacts and/or terminals, are arranged in the edge region. Non-transparent conductor paths, which fulfil a heating function, are laid optically transparent over a central region. When an electric current is applied, the conductor paths cause the laminar body to be heated, which can be adjusted either uniformly over the surface and/or in individual regions of the surface. For example, the heating power can be set higher opposite the eyes than, for example, in the nose region.

DE 1 951 643 A discloses a pair of safety goggles having a clear lens. Electric heating elements are formed inside the clear lens, which can be connected by means of electric conductors to a power source that is arranged in/on a frame of the clear lens or a retaining strap. Preferably, the heating elements and/or conductors can be obtained by metal vapor deposition, in particular of goggle portions that extend in the eye areas. They may also be otherwise formed, for example by resistance wires or printed metal layers. The clear lens is preferably equipped with contact nipples or the like in connection with the heating elements, to which power sources that are fixed to the frame or the strap can be detachably plugged via electrical conductors. The vapor deposition layers, metal wires or the like that serve as heating elements can extend in or on the printed circuit boards formed on the clear lens. The power sources are fixed directly or by means of receptacles to the frame and/or the clear lens or the retaining strap. These glasses have a high energy consumption in operation and are also bulky.

DE 27 18 679 A1 discloses a heatable viewing lens, in particular for ski goggles, which is provided with a heating element. The heating element is connected to a power source via a humidity sensor. It is convenient if the heating element is formed by an electrically conductive coating which is applied to a foil that is attached to the inner surface of the viewing lens. Two surface contacts are applied to the coating to which an electrical voltage can be applied. This viewing lens has proven itself in practice.

SUMMARY OF THE INVENTION

It is an object of the invention to provide an improved goggle lens and goggles. In particular, the goggle lens and goggles should offer the wearer a high level of comfort and be particularly user-friendly.

This object is achieved according to the invention by a goggle lens comprising a main body, comprising at least one transparent, electrically conductive coating which covers the main body at least partly, comprising electrical contact means which partly cover the at least one coating, are in electrical connection with the at least one coating and partly form at least two electrical heating zones which are openable independently of each other; and comprising electrical conductor paths which are electrically connected to the contact means for energizing the contact means, wherein at least one of the conductor paths runs partly on an inner side of the goggle lens and partly on an outer side of the goggle lens and goggles comprising at least one such goggle lens. The essence of the invention is at least one coating which covers a main body of the goggle lens and is in electrical connection with electrical contact means for electrically heating the goggle lens. The contact means and the at least one coating are capable of conducting electric current or electric voltage.

The arrangement of at least one conductor path on both sides or of at least one contact means enables a particularly uniform heating of the goggle lens. It is expedient if each conductor path runs on the inner side of the goggle lens and on the outer side of the goggle lens.

The heating zones that are operable independently from each other are preferably operable by the circuit, such as controllable or adjustable. For example, the heating powers of the heating zones differ from one another during operation. For example, at least one heating zone is turned on, while at least one other heating zone is turned off at the same time. Operation at reduced or full heating power is possible. The heat output of each heating zone can, for example, be between 0% and 100%. It is preferably continuously adjustable.

Another preferred embodiment of the goggle lens comprises a main body, at least one transparent, electrically conductive coating covering the main body at least partly, and electrical contact means which cover the at least one coating partly and are in electrical connection with the at least one coating and form at least one electrical heating zone. The goggle lens further has a sensor board comprising at least one spring contact for the electrical connection to conductor paths, wherein the contact means are electrically connected or connectable to at least one electrical or electronic circuit.

The at least one spring contact ensures a functionally reliable electrical connection between the sensor board/goggle lens board and the conductor paths. The at least one spring contact is in particular capable of establishing a secure electrical connection there despite the curvature of the main body or the goggle lens. It preferably has at least one resiliently displaceable, electrically conductive spring contact means, such as a small plate, pin or the like.

For example, the goggle lens is designed as a continuous lens, i.e. a full-vision lens, which extends in front of both eyes of the goggle wearer when the goggles are worn. Alternatively, it is designed as a goggle lens which only extends in front of exactly one eye of the goggle wearer when the goggles are worn. The goggles then have two separate goggle lenses arranged next to each other. The goggle lens is transparent and preferably multi-layered. For example, it is tinted. Alternatively, it is colorless. It is convenient if a goggle frame or at least a frame part is connected to the goggle lens. Advantageously, at least one ventilation opening is arranged in the goggle lens and/or adjacent thereto.

It is advantageous if the main body is made of glass and/or plastic material, such as polycarbonate. It is preferably formed by injection molding. Preferably, it is a molded body.

The at least one coating is preferably continuous. Alternatively, it is formed by separate coating regions, for example. The at least one coating preferably covers the main body on at least one side at least partly, preferably at least largely, preferably completely. It is convenient if the coating is located on the inside and/or outside of/on the main body, i.e. on/on the side facing towards and/or away from the goggle wearer when the goggles are worn. It is in direct or indirect connection with the main body.

The at least one coating is preferably formed by wires, in particular nanowires, and/or particles. It is convenient if the at least one coating comprises electrically conductive metal, such as silver. Preferably, the coating is formed by or with silver nanowires.

The electrical contact means are preferably configured to be flat and preferably elongated. They are, for example, strip-shaped, bar-shaped or the like. The contact means extend, for example, at least partly in a straight, curved, arc-shaped or similar manner Combinations are possible. The contact means are preferably formed from an electrically conductive metal and are electrically connected or connectable to at least one electrical or electronic circuit, for example directly or indirectly, forming a power circuit. It is convenient if they are electrically connected or connectable, directly or indirectly, to at least one energy source or power source, such as a battery, rechargeable battery or the like. The rechargeable battery is preferably electrically rechargeable without cables or contact.

Each electrical heating zone of the goggle lens covers the main body. It is formed by the associated contact means and advantageously the at least one coating. Each electrical heating zone is preferably formed by at least two electrical contact means which are preferably arranged opposite each other, advantageously at different heights of the goggle lens, such as at the bottom and at the top. By means of different heating zones, a homogeneous or targeted heating of the goggle lens is possible. It is useful if heating cycles take place depending on the situation and/or are time-controlled.

The electrical conductor paths are preferably configured to be elongated and advantageously run parallel to each other partly. They are made of an electrically conductive metal and are capable of conducting electric current or voltage. The conductor paths are electrically connected or connectable to at least one electrical or electronic circuit, for example directly or indirectly, forming a power circuit. It is useful if they are directly or indirectly electrically connected or connectable to at least one energy source or power source, such as a battery, rechargeable battery or the like.

It is convenient if at least one electrical/electronic component is replaceable.

Advantageously, for wearing the goggles, the latter have at least one head retaining means for retaining the at least one goggle lens on the head of the goggle wearer. The at least one head retaining means is designed, for example, as a headband, goggle temple or the like. It is advantageous if the headband comprises a length adjustment means. It is convenient if the electrical or electronic circuit is arranged at a distance from the goggle lens, for example on the head retaining means of the goggles and preferably opposite the goggle lens. This ensures a particularly good weight distribution and thus an extremely high wearing comfort.

Further advantageous embodiments of the invention are set forth in the following.

The heating zones which are arranged next to each other are, for example, separate from each other. Alternatively, they are directly adjacent to each other. It is useful if there are between two and five, preferably two or three, heating zones.

The conductor paths and/or contact means which are printed on can be manufactured in a particularly cost-effective and functionally reliable manner. They only require a small amount of space.

The internal anti-fog overcoating which is transparent and water-absorbing is preferably continuous. Alternatively, it is formed by individual regions. The anti-fog overcoating prevents or slows down fogging of the goggle lens when the at least one heating zone is currently inactive, for example due to an empty power source. It is convenient if the anti-fog overcoating covers the at least one coating and preferably the contact means at least partly. It has a free side which faces the wearer of the goggles when the goggles are worn. It is convenient if the anti-fog overcoating is a wet chemical coating. It is preferably in indirect contact with the main body. It is advantageous if it is in direct contact with the at least one coating.

It is expedient if the goggle lens has at least one sensor for a current application when sensing a deviation from a setpoint value or setpoint value range. The at least one sensor enables a targeted, demand-dependent application of current to the contact means. For example, it is capable of sensing a saturation of the anti-fog overcoating, a prevailing temperature of the goggle lens and/or its adjacent environment and/or a prevailing humidity of the goggle lens and/or its adjacent environment. It is convenient if the at least one sensor is arranged directly on the goggle lens. Alternatively, it is arranged at a distance from, but adjacent to, the goggle lens. The at least one sensor is preferably electrically connected or connectable to the circuit, for example directly or indirectly. It is capable of converting the sensed quantity/quantities into a corresponding, in particular processable, electrical signal.

The at least one hard layer which is transparent and covers the main body at least partly leads to a particularly scratch-resistant goggle lens. Damage to the goggle lens can thus be avoided or reduced. The at least one hard layer is in direct or indirect contact with the main body. It is in direct or indirect connection with the at least one coating. It is arranged on the inside and/or outside in relation to the main body. Each hard layer has a free side which faces towards or away from the goggle wearer when the goggles are worn.

The main body is curved at least partly, such as two-dimensionally or three-dimensionally, preferably strongly. It is convenient if the at least one coating, anti-fog overcoating, if present, hard layer, if present, and at least one heating zone follows said curvature.

It is advantageous if the goggle lens is directly equipped with at least one electronics component and/or sensor component. The electronic component is, for example, part of the circuit. Alternatively, it forms the circuit completely. The electronic component is designed as a microcontroller, for example. The sensor component is, for example, a constituent part of the at least one sensor. Alternatively, it completely forms the at least one sensor.

It is advantageous if the goggles comprise a headband for retaining the goggles on a head of a wearer of the goggles, wherein the headband has a flexible, elastic, elongated supporting body and electrical connection lines for connecting a power source to electrical contact means, wherein the connection lines are arranged on the supporting body at least partly such that they are able to change their length in a longitudinal direction of the supporting body. The connection lines allow the size of the headband to be adjusted to the wearer of the goggles, which is particularly user-friendly. It is convenient if the connection lines form a flat band conductor and preferably run parallel to one another, such as meandering, serpentine, zigzag or the like, at least partly. They may run at least partly at a distance from one another or abut one another. They are advantageously inextensible and preferably electrically insulated at least along their longitudinal extension. Advantageously, the connection lines are fixed to the supporting body partly.

In the following, preferred embodiments of the invention are described by way of example with reference to the attached drawing.

DESCRIPTION OF THE PREFERRED EMBODIMENTS

Parts that are corresponding to each other are marked with the same reference signs in FIGS. 1 to 16. Details of the preferred embodiments explained in more detail below may also constitute an invention in their own right or form part of a subject-matter of an invention.

Figure 1:
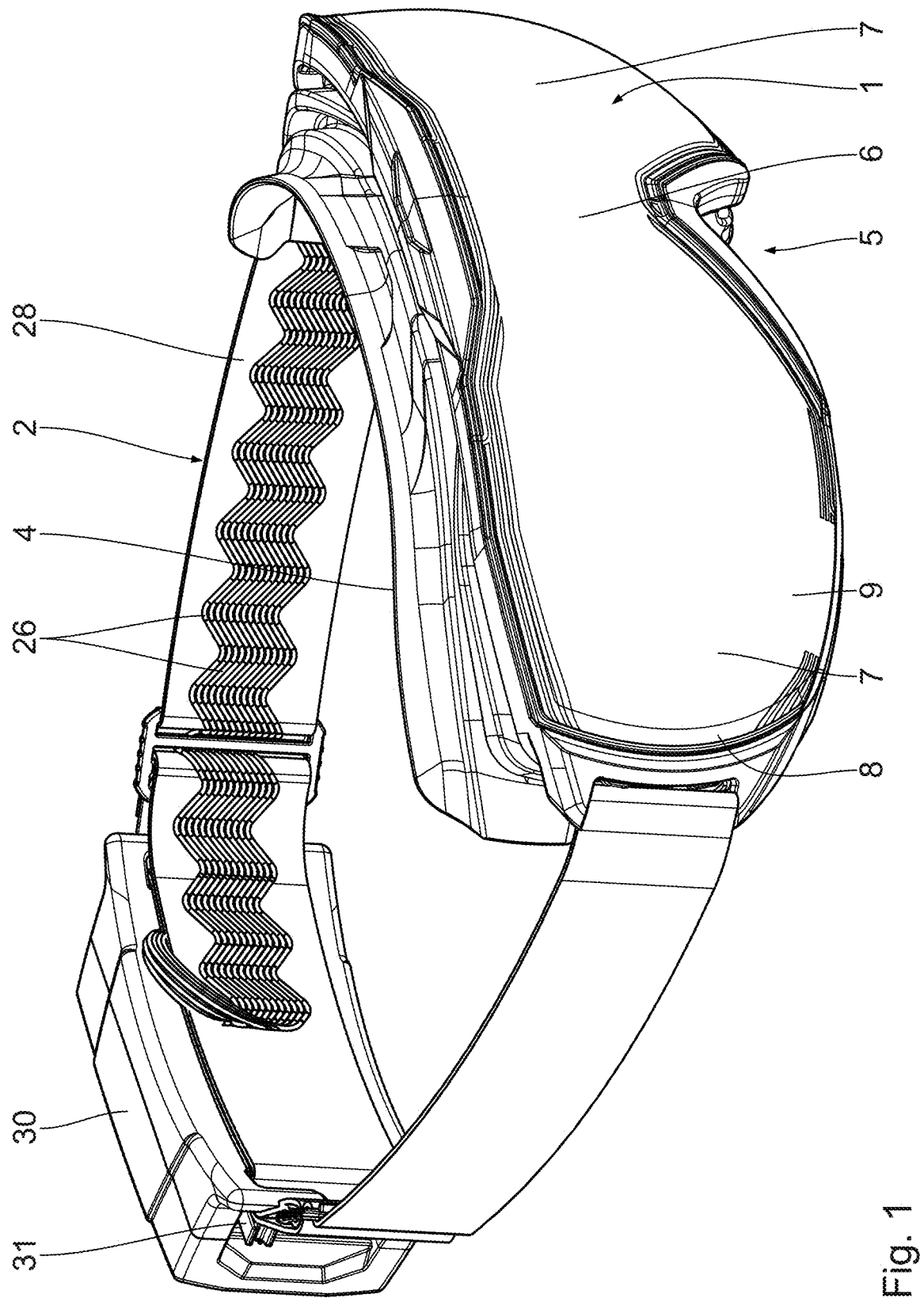
FIG. 1 shows a perspective view of a pair of goggles according to the invention with a goggle lens of the invention.
Figure 2:
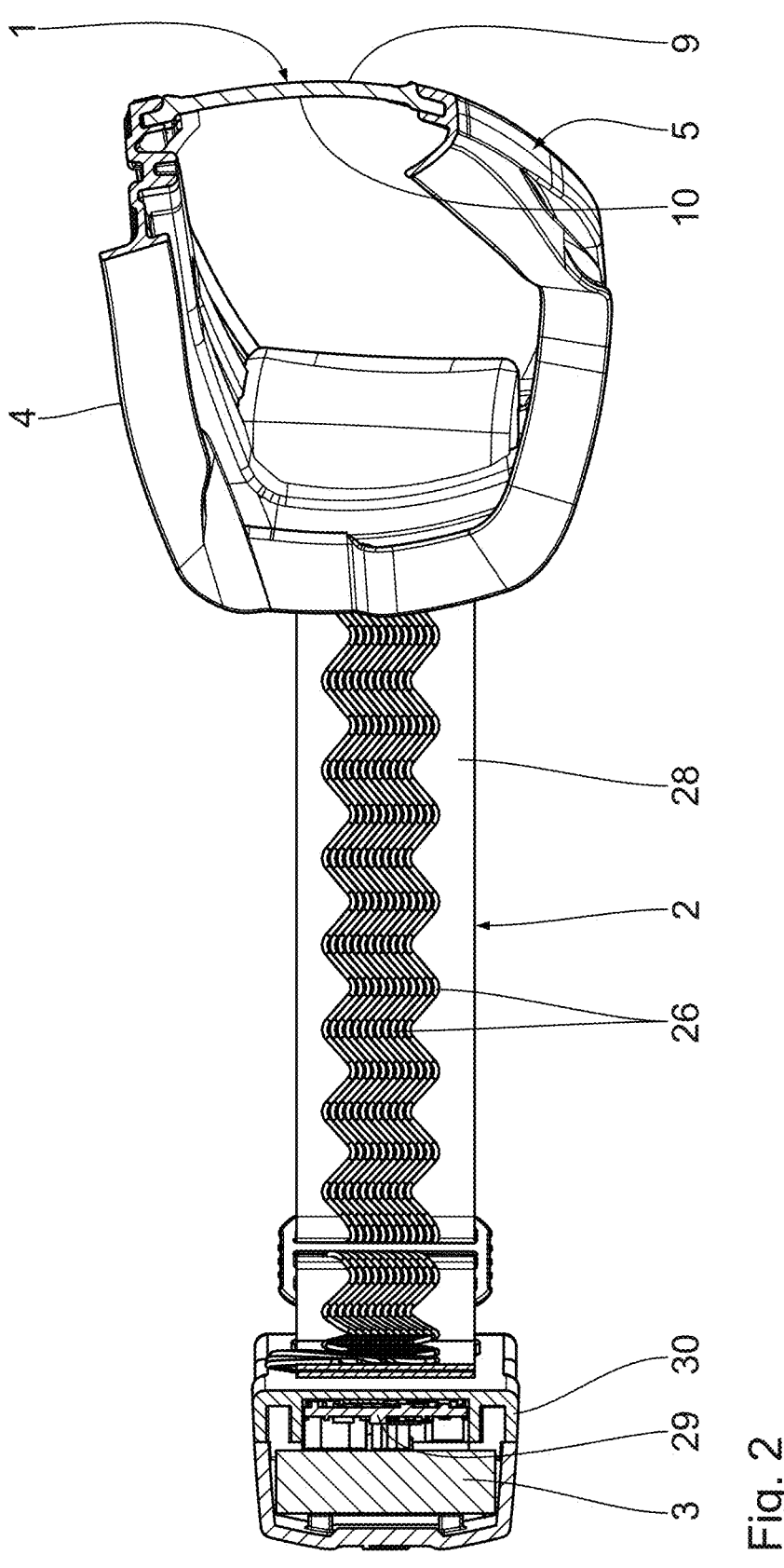
FIG. 2 shows a section through the goggles illustrated in FIG. 1 along a first main plane of the goggles.
Figure 3:
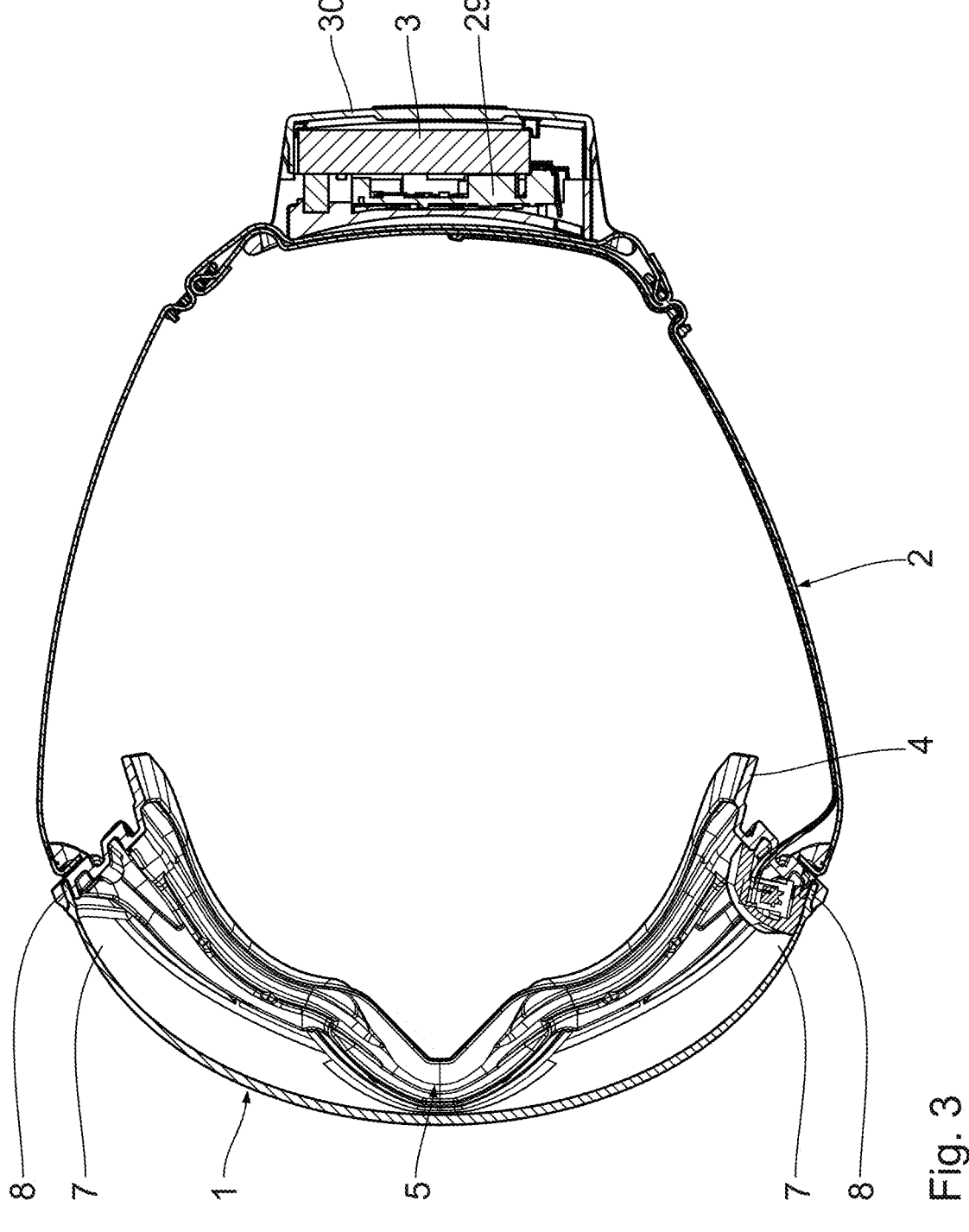
FIG. 3 shows a section through the goggles shown in FIG. 1 along a plane perpendicular to the main plane shown in FIG. 2.

A pair of goggles shown in its entirety in FIGS. 1 to 3 comprises an electrically heatable full-vision goggle lens 1 and a headband 2 that is connected to the goggle lens 1, as well as a power source 3 that is arranged on the headband 2 for electrically heating the goggle lens 1.

A sealing body 4 is arranged on the edge of the goggle lens 1 for contact with a face of a goggle wearer (not shown). The sealing body 4 is elongated and preferably closed in the circumferential direction. It is flexible and made, for example, of foam, rubber or the like. The sealing body 4 spatially bounds an inner space together with the goggle lens 1.

The goggle lens 1 has a central region 6 above a central nose recess 5 and a side region 7 in each case to the side of the central region 7, each of which extends to a side edge 8 of the goggle lens 1. Furthermore, the goggle lens 1 has an outer side 9 that faces away from the wearer when the goggles are worn and an inner side 10 that faces the wearer. The goggle lens 1 is strongly curved.

The goggle lens 1 comprises a goggle lens main body 11 and a transparent, electrically conductive coating 12 that is directly arranged thereon, as well as an anti-fog overcoating 13 that is arranged directly above the latter. The coating 12 is formed by a plurality of silver nanowires (AgNW). Opposite the coating 12, a hard or scratch-resistant layer 14 is preferably arranged directly on the main body 11. The hard layer 14 forms the outer side 9 and is thus designed as an outer layer. The anti-fog overcoating 13, on the other hand, forms the inner side 10 and is designed as an inner layer (see FIG. 12).

Figure 13:
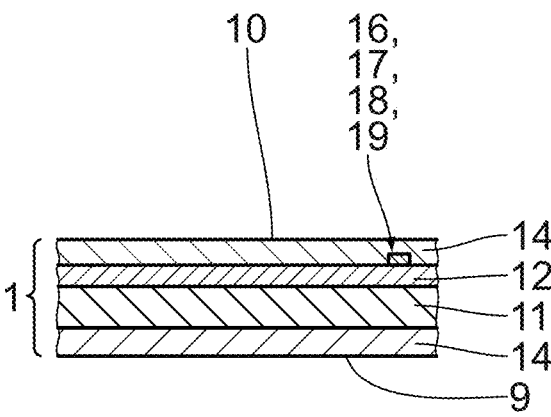

According to an alternative embodiment, instead of the anti-fog overcoating 13, a further/second hard layer 14 is provided (FIG. 13).

Figure 14:
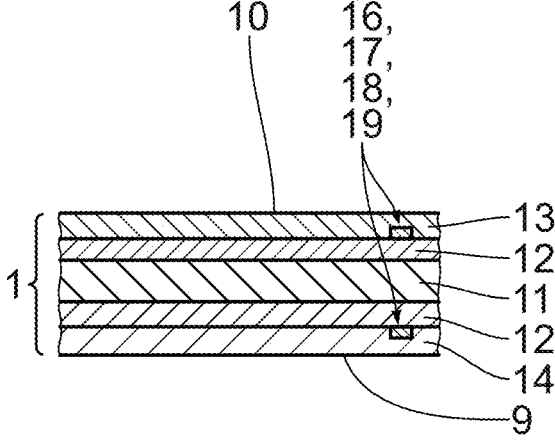

According to an alternative embodiment, a transparent, electrically conductive coating 12 is arranged directly on each side of the main body 11. A first coating 12 is directly covered by a hard layer 14 forming the outer side 9, while the other, second coating 12 is directly covered by an anti-fog overcoating 13 forming the inner side 10 (FIG. 14).

Figure 15:
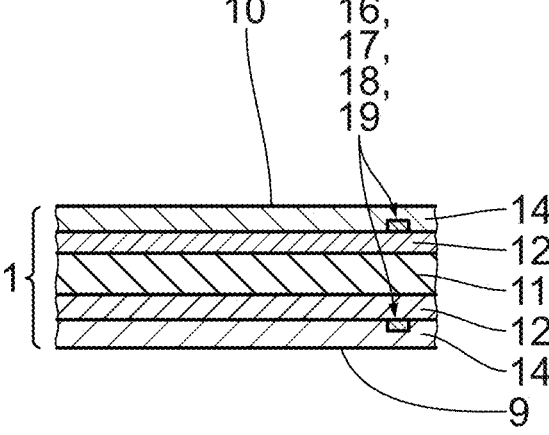

Alternatively, both transparent, electrically conductive coatings 12 are each directly covered by a hard layer 14 (FIG. 15). A first hard layer 14 forms the outer side 9, while the other/second hard layer 14 forms the inner side 10.

Combinations or a different layer structure is/are alternatively possible.

Figure 7:
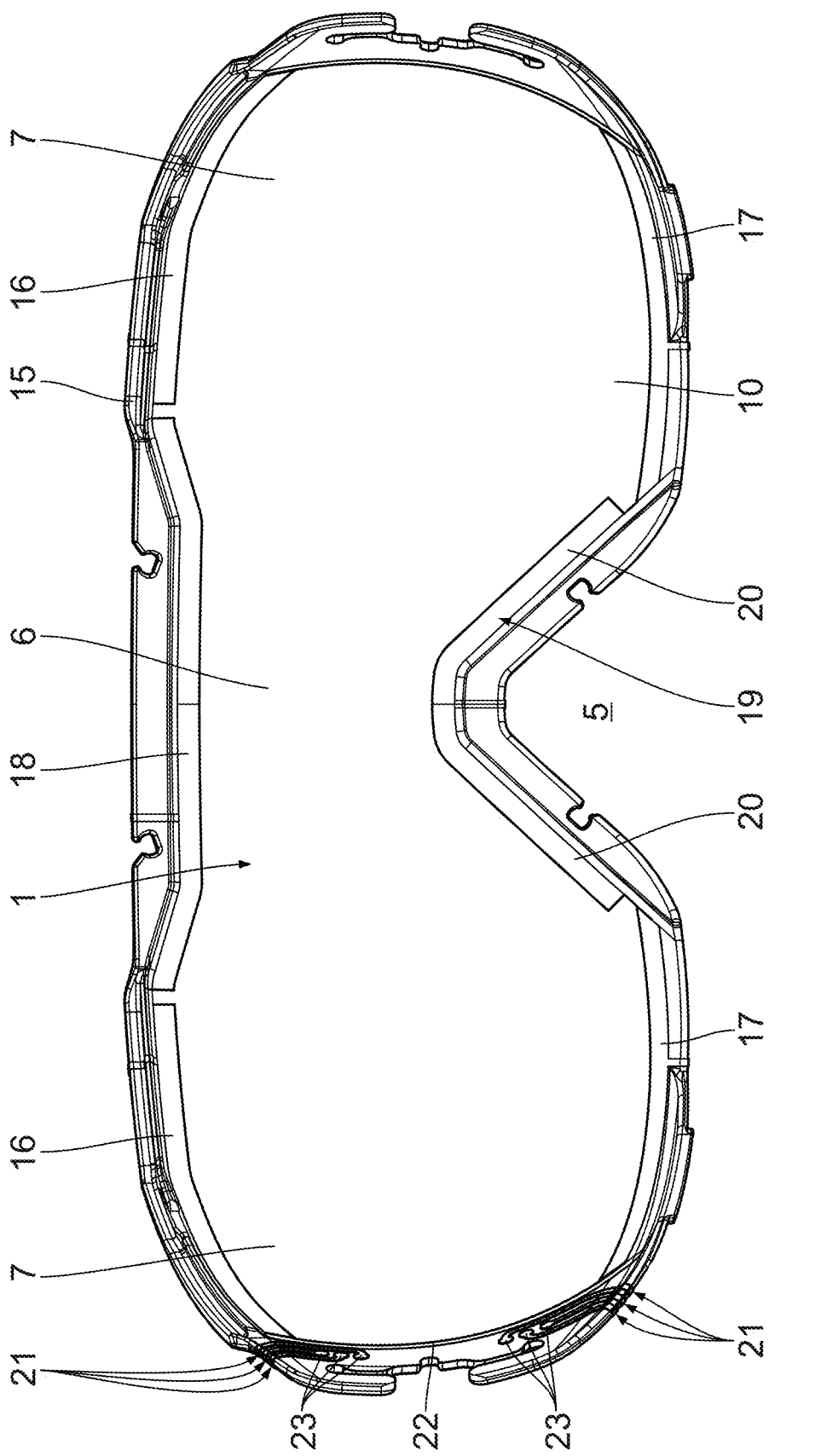
FIG. 7 shows a view from the inside onto the goggle lens of the goggles illustrated in FIGS. 1 to 3.

For example, as shown in FIG. 7, the goggle lens 1 has a plurality of elongate electrical contact means which extend adjacent to or along a circumferential edge 15 of the goggle lens 1 in the circumferential direction of the goggle lens 1. In each side region 7, an upper lateral contact means 16 and a lower lateral contact means 17 are arranged. An upper, central contact means 18 and a lower, central contact means 19 are arranged in the central region 6. The lower, central contact means 19 follows the nose recess 5 and has two legs 20 that run at an angle towards one another.

The contact means 16, 17, 18, 19 are spaced apart in the circumferential direction. The upper, lateral contact means 16 and the upper, central contact means 18 run (essentially) at a common height, while the lower, lateral contact means 17 run at a common height. The upper lateral contact means 16 extend above the lower lateral contact means 17, i.e. at a greater height than the lower lateral contact means 17. They are arranged laterally or in a lateral direction of the goggle lens 1 (essentially) not offset from one another. The upper, central contact means 18 runs above the lower, central contact means 19, i.e. at a greater height than the lower, central contact means 19. They are arranged laterally or in a lateral direction of the goggle lens 1 (essentially) not offset from one another. The contact means 16, 17, 18 and 19 arranged in each region 6, 7 respectively form an electrical contact means pair. There are three pairs of contact means. The contact means 16, 17, 18 or 19 are in direct electrical connection with the coating 12 and are preferably covered by or embedded in the anti-fog overcoating 13. In particular, they are printed on the coating 12 at least to a certain extent and in particular on the edge side.

Figure 6:
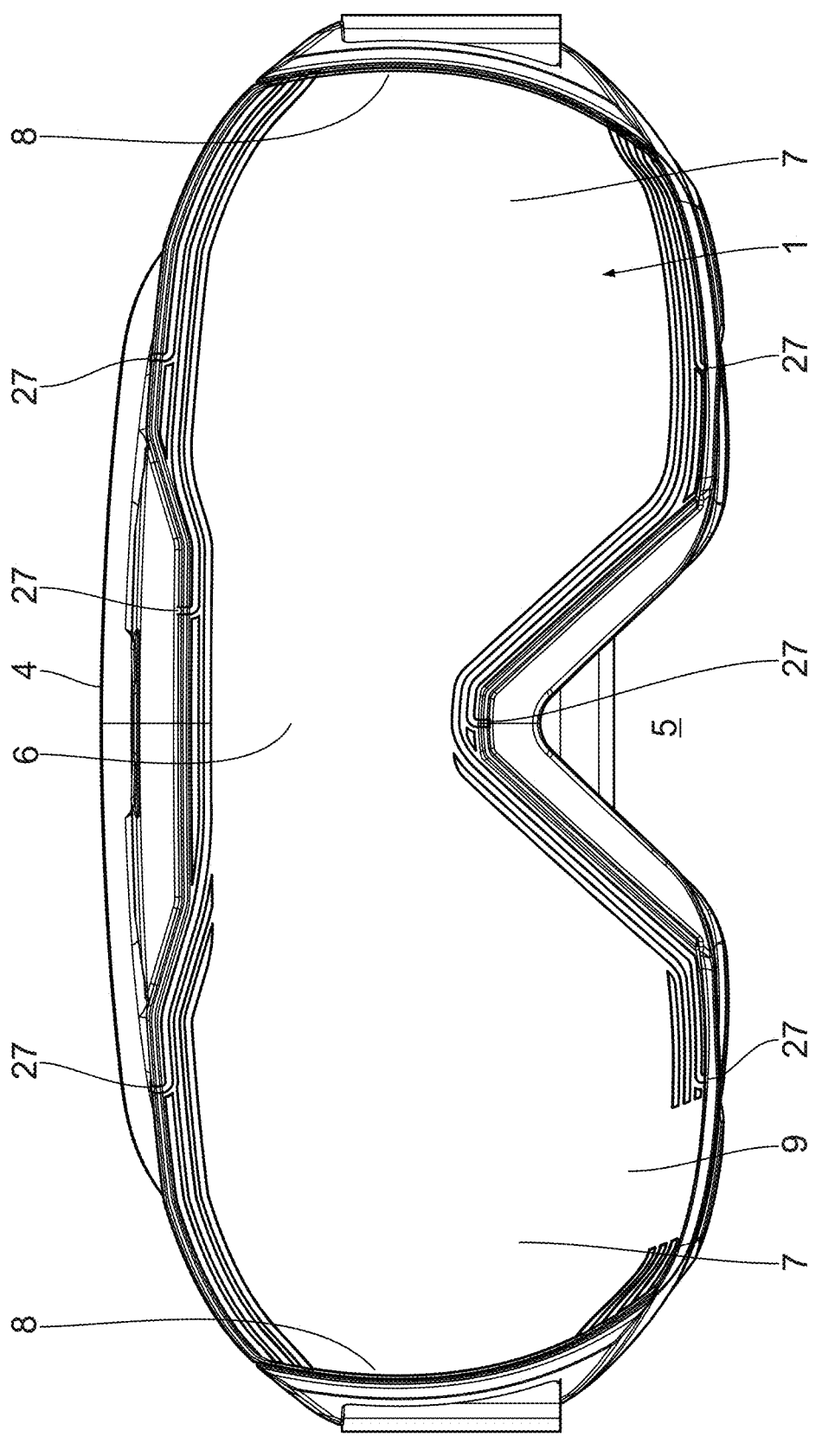
FIG. 6 shows an external view onto the goggle lens shown in FIGS. 1 to 3.
Figure 8:
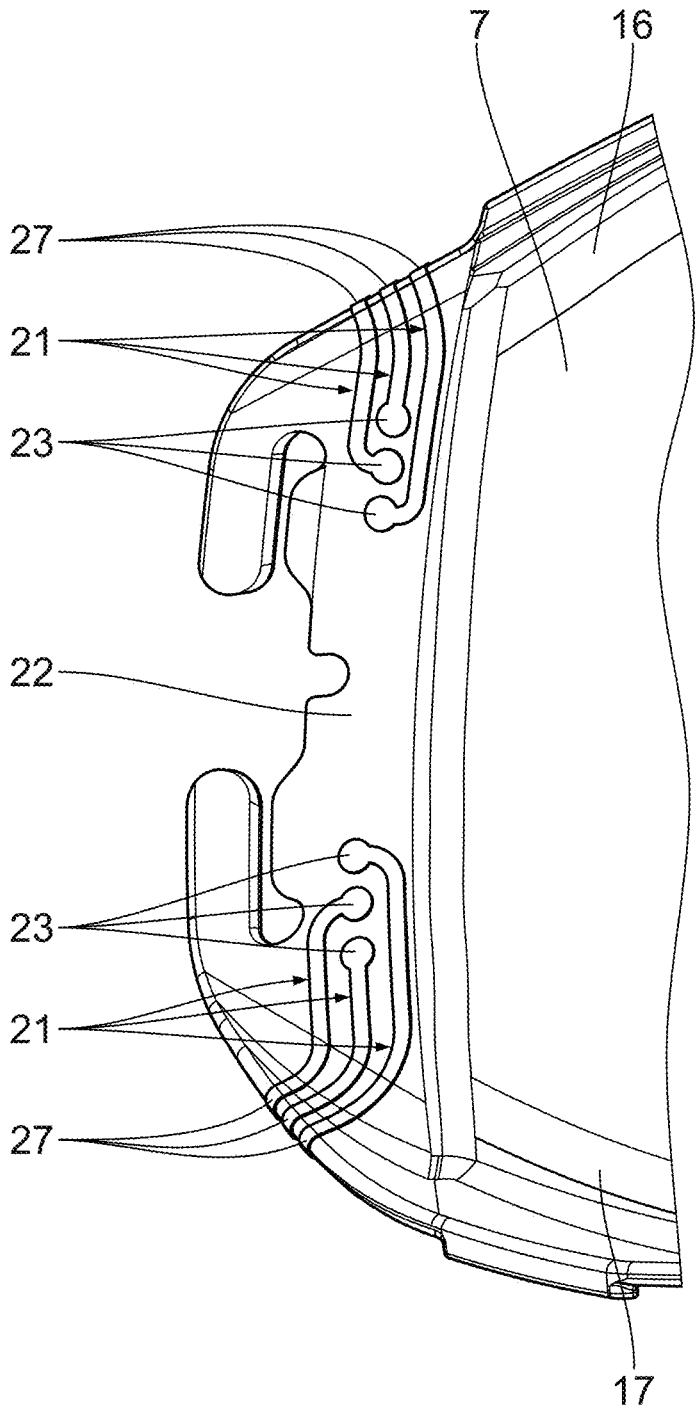
FIG. 8 shows a side region of the goggle lens of the goggles shown in FIGS. 1 to 3.
Figure 9:
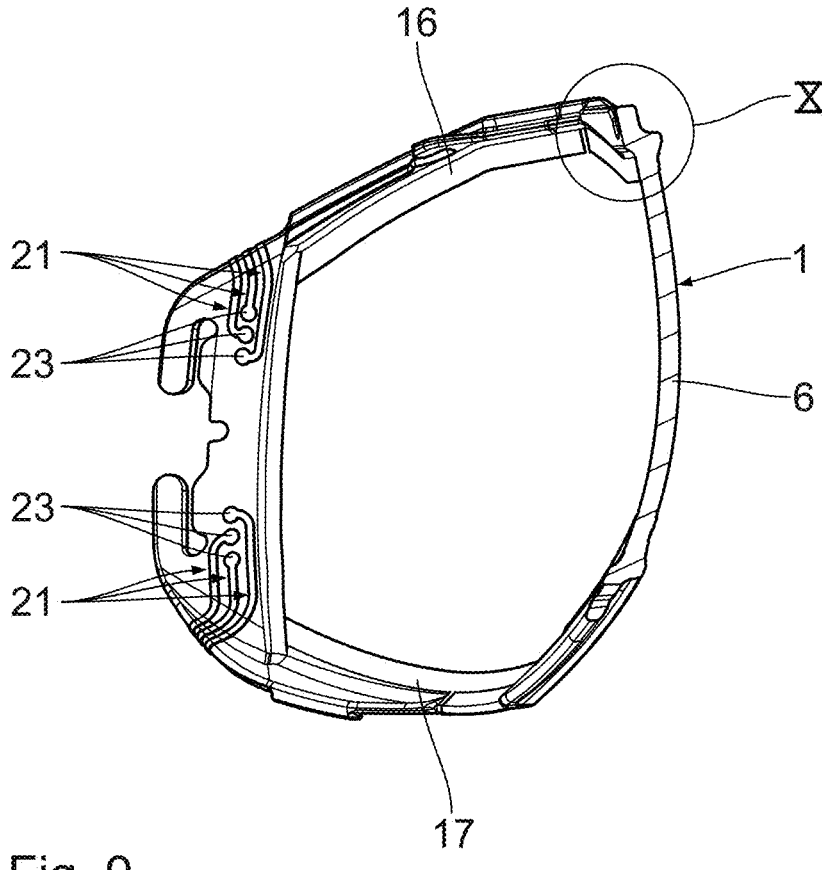
FIG. 9 shows a section through the goggle lens of the goggles illustrated in FIGS. 1 to 3.
Figure 10:
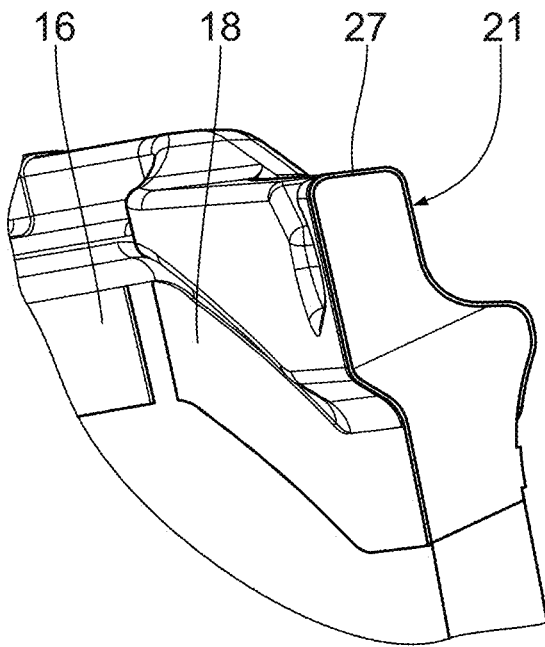
FIG. 10 shows the detail X marked in FIG. 9.

Each contact means 16, 17, 18 or 19 is in electrical connection with its own electrical conductor path 21, which extends along the circumferential edge 15 and ends in a side end region 22 of the goggle lens 1 to form an enlarged, flat, exposed contact point 23 (FIGS. 7, 8). Each conductor path 21 runs on the inside and outside in relation to the main body 11 or the goggle lens 1. FIG. 6 shows corresponding side changes 27 of the conductor paths 21 between the inner side 10 and the outer side 9 of the goggle lens 1. At each side change 27, the respective conductor path 21 runs around the outside of the main body 11 or its outer edge (FIGS. 9, 10).

In the embodiment according to FIG. 13, the contact means 16, 17, 18 and 19 are again in direct electrical connection with the coating 12 and are covered by the further hard layer 14, i.e. the layer that forms the inner side 10.

First contact means 16, 17, 18 or 19 are in direct electrical connection with the first coating 12 in the embodiment according to FIG. 14 and are covered by the hard layer 14. Second contact means 16, 17, 18 or 19 are in direct electrical connection with the second coating 12 and are covered by the anti-fog overcoating 13.

First contact means 16, 17, 18 or 19 are in direct electrical connection with a first coating 12 in the embodiment according to FIG. 15 and are covered by the first hard layer 14.

Second contact means 16, 17, 18 or 19 are in direct electrical connection with a second coating 12 and are covered by the second hard layer 14.

Figure 4:
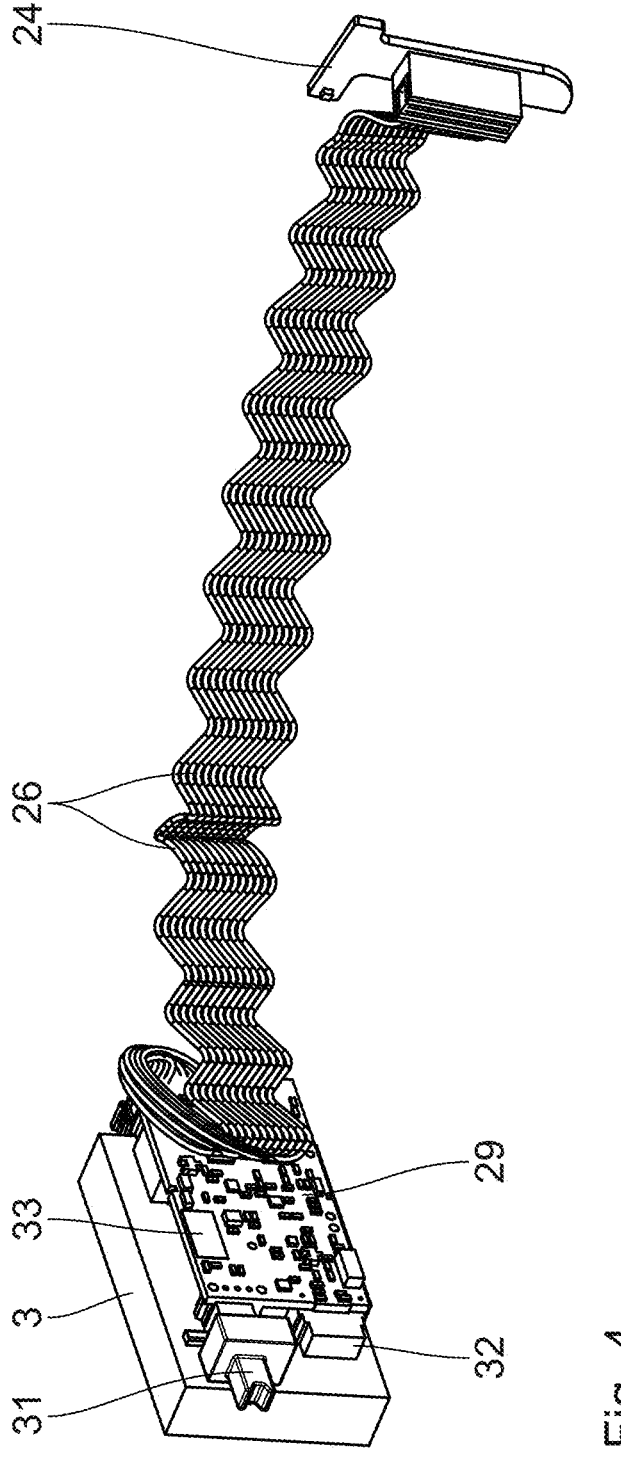
FIG. 4 shows a perspective view showing insulated electrical or electronic components of the goggles shown in FIGS. 1 to 3.
Figure 5:
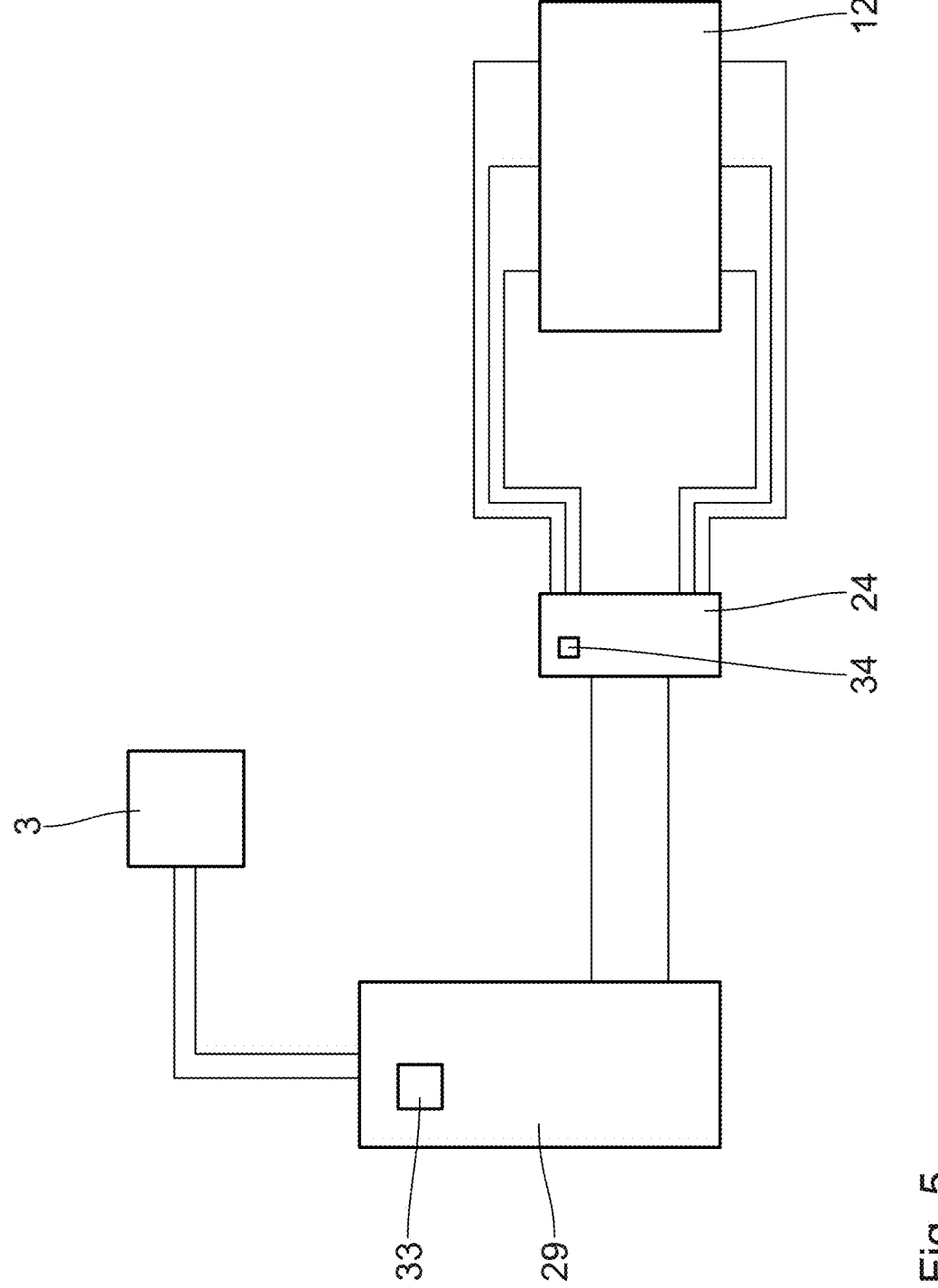
FIG. 5 shows a simplified block diagram illustrating the interaction of the electrical and electronic components of the goggles shown in FIGS. 1 to 3.

The goggle lens 1 also comprises/carries a sensor/goggle lens board 24 (FIG. 4, 11). The sensor board 24 is arranged on the inside in the side end region 22 and has pin-like spring contacts 25, at least one sensor 34 and preferably its own microcontroller. The spring contacts 25 are of identical design and are resiliently variable in length. Each spring contact 25 projects vertically from a main plane 35 of the sensor board 24 and is in electrical connection with a contact point 23 of a respective conductor path 21. Due to the curvature of the goggle lens 1 in the side end region 22, the spring contacts 25 have different lengths; in particular, the length of upper spring contacts 25 increases from top to bottom and the length of lower spring contacts 25 increases from bottom to top. The sensor board 24 is preferably covered by a cover.

Each spring contact 25 is in electrical connection with two electrical connection lines 26 (FIG. 1, 2, 4, 11), which are electrically connected to the sensor board 24. The connection lines 26 run from the sensor board 24 via the headband 2 to the power source 3. They are arranged on the inside of a supporting body 28 of the headband 2 and are arranged next to each other in a transverse or width direction of the headband 2. The connection lines 26 run parallel to each other. They are arranged in a meandering pattern and are thus able to follow a change in the length of the headband 2, such as an increase or decrease in length.

The connection lines 26 are fixed locally to the supporting body 28, in particular by means of, preferably transparent, retaining threads. The retaining threads are made of nylon, for example. They are preferably sewn to the supporting body 28 and run around the respective connection lines 26. The retaining threads that fix a connection line 26 are arranged at a distance from each other along this connection line 26.

Each connection line 26 preferably has a diameter between 0.1 mm and 0.5 mm (without insulation) and between 0.5 mm and 0.8 mm (with insulation). In the unstretched state of the headband 2, the distance between two adjacent extreme points, i.e. a minimum and a maximum, of the connection lines 26 is favorably between 5 mm and 15 mm.

The connection lines 26 are electrically connected to a main board 29 (FIG. 2, 4), which is arranged adjacent to the power source 3. The main board 29 and the power source 3 are arranged together in a housing 30. The housing 30 carries an on/off switch 31 which is manually operable and, in an on setting, allows a power connection between the power source 3 and the main board 29. In an off setting, the on/off switch 31 interrupts the power connection therebetween. Further, the housing 30 carries a charging socket 32, which is for example configured as a USB socket, in particular a USB-C socket. The main board 29 in turn carries a microcontroller 33 for processing electrical sensor data or signals from the at least one sensor 34 and for applying current to the contact means 16, 17, 18 or 19.

The use of the goggles is described in more detail below.

When the goggles are worn, the goggle lens 1 extends in front of the wearer's eyes and runs around some regions of the wearer's face. The nose of the goggle wearer engages in the nose recess 5. The housing 30 is located in the region of the back of the wearer's head opposite the goggle lens 1.

In the on setting of the on/off switch 31, current is applied to the microcontroller 33 from the power source 3. The microcontroller 33 receives corresponding electrical sensor signals from the at least one sensor 34 via the connection lines 26. If the microcontroller 33 determines that at least partial heating of the goggle lens 1 is necessary, electrical current is fed from the power source 3 via the respective connection line 26 to the sensor board 24, which applies current via the respective spring contact 25 to the associated conductor path 21 and thus to the associated contact means 16, 17, 18 or 19. The electric current thus reaches the coating 12 via the respective contact means 16, 17, 18 or 19. It flows via the coating 12, forming a respective electrical heating zone, to the associated opposite contact means 16, 17, 18 or 19, from where it flows back to the main board 29 via the respective conductor path 21 and the associated spring contact 25 as well as the corresponding connection line 26.

Figure 12:
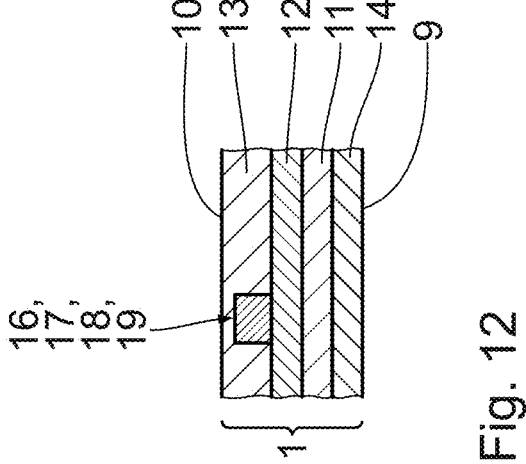
FIG. 12 shows a sectional view illustrating a possible construction of the goggle lens of the goggles shown in FIGS. 1 to 3, FIGS. 13 to 15 show sectional views, each showing an alternative construction of the goggle lens of the goggles shown in FIGS. 1 to 3.
Figure 11:
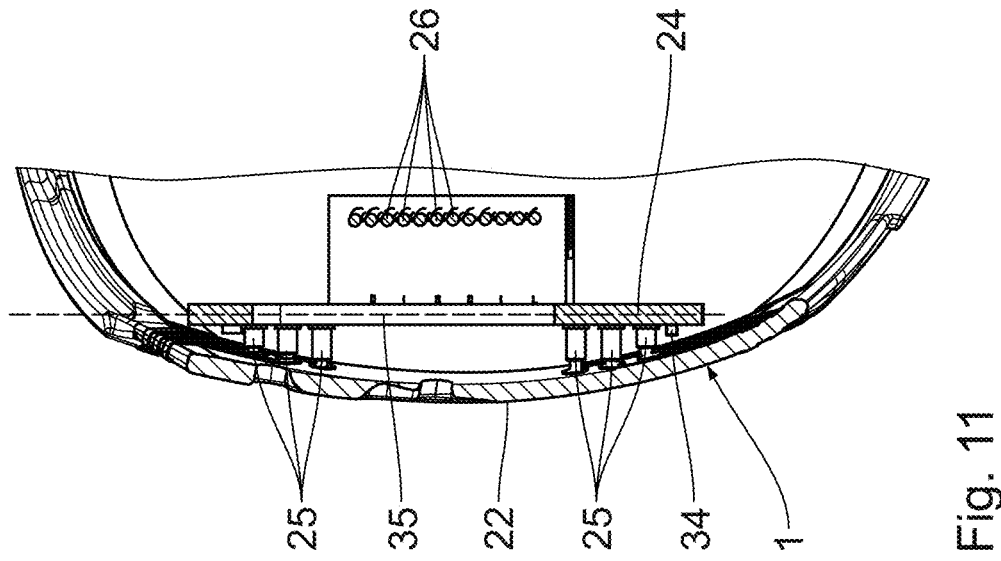
FIG. 11 shows a side view of the goggle lens shown in FIGS. 1 to 3, which also shows a sensor board.

In the embodiment according to FIG. 12, the heating power of each heating zone is set such that the anti-fog overcoating 13 is heated from the inside at maximum saturation and the moisture is driven out of it. Saturation of the anti-fog overcoating 13 thus does not occur, which permanently prevents fogging and reduces the heating power to a minimum. The microcontroller 33 of the main board 29 adjusts the heating current accordingly in order to dehumidify the anti-fog overcoating 13. Accordingly, current is supplied to the heating zones only when required. It is expedient if the microcontroller 33 of the main board 29 has/uses an evaluation algorithm for evaluating the sensor signals. The moisture or saturation of the anti-fog overcoating 13 or goggle lens 1 is sensed accordingly by the at least one sensor 34. The power source 3 supplies the heating zones and the main board 29 with electrical current during operation.

In the embodiments according to FIGS. 13 and 15, the heating prevents condensation of moisture on the inner side 10, which is formed on the hard layer 14 in each case. The hard layers 14 are each heated from the inside. The heating is otherwise preferably carried out according to the embodiment of FIG. 12, the description of which is referred to.

In the embodiments according to FIGS. 14, 15, the main body 11 is heated on both sides. In the embodiment according to FIG. 14, both the anti-fog overcoating 13 and the hard layer 14 are heated from the inside. In the embodiment according to FIG. 15, both hard layers 14 are heated from the inside.

In the embodiment according to FIG. 14, the heating power of each heating zone is set such that the anti-fog coating 13 is heated from the inside at maximum saturation and the moisture is driven out of it. Saturation of the anti-fog overcoating 13 is thus prevented, which permanently prevents fogging and reduces the heating power to a minimum. The heating is otherwise preferably carried out according to the embodiment shown in FIG. 12, the description of which is referred to.

Figure 16:
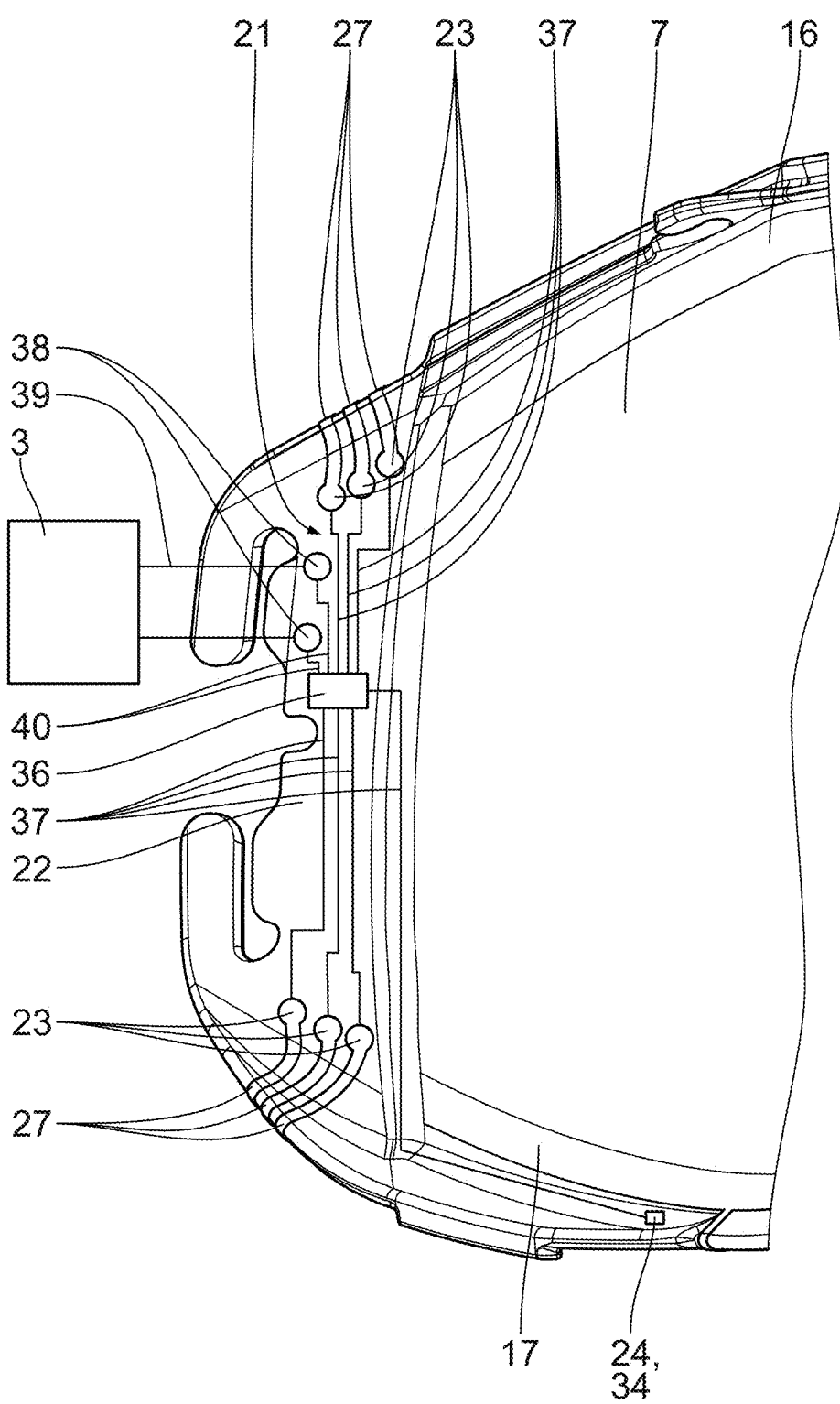
FIG. 16 shows a side region of an alternative goggle lens of the goggles shown in FIGS. 1 to 3

In the following, an alternative design of the goggle lens 1 is described with reference to FIG. 16. In comparison with the goggle lens 1 according to FIGS. 8, 11, the description of which is referred to, the goggle lens 1 according to this embodiment is directly equipped with the at least one sensor 34, which is arranged in an edge region of the goggle lens 1, such as laterally at the bottom. Furthermore, the goggle lens 1 is directly equipped with a microcontroller 36, which is arranged in the side end region 22 of the goggle lens 1. The microcontroller 36 constitutes, for example, the microcontroller of the sensor board 24 and/or the microcontroller 33 of the main board 29.

The at least one sensor 34 and the contact points 23 are electrically connected to the microcontroller 36 via electrical connection lines 37. Furthermore, two electrical connection points 38 are arranged in the side region 22, which are connected or connectable to the power source 3 via electrical lines 39 and are electrically connected to the microcontroller 36 via electrical lines 40. The connection lines 37 and lines 40 are also applied directly to the goggle lens 1.

In operation, the microcontroller 36 is supplied with current from the power source 3. The microcontroller 36 receives corresponding electrical signals from the at least one sensor 34 via the associated connection line 37. If the microcontroller 36 determines that at least partial heating of the goggle lens 1 is necessary, electrical current is conducted via the respective connection line 37 to the associated contact means 16, 17, 18 or 19 via the associated conductor path 21, from where the electrical current reaches the coating 12. It flows via the coating 12, forming a respective electrical heating zone, to the associated opposite contact means 16, 17, 18 or 19, from where it flows back to the microcontroller 36 via the respective conductor path 21 and the corresponding connection line 37. The heating via the heating zones is essentially carried out analogously to the corresponding previous embodiment to which reference is made.

The invention claimed is:

1. A goggle lens
   a) comprising a main body,
   b) comprising at least one transparent, electrically conductive coating which covers the main body at least partly,
   c) comprising electrical contact means which
      i) partly cover the at least one coating,
      ii) are in electrical connection with the at least one coating, and
      iii) partly form at least two electrical heating zones which are openable independently of each other; and
   d) comprising electrical conductor paths which are electrically connected to the contact means for energizing the contact means,
wherein
   e) at least one of the conductor paths runs partly on an inner side of the goggle lens and partly on an outer side of the goggle lens,
      wherein in case of the at least one conductor path that runs partly on the inner side of the goggle lens and partly on the outer side of the goggle lens, there is a side change between the inner side of the goggle lens and the outer side of the goggle lens.

2. The goggle lens according to claim 1, wherein the heating zones are arranged next to each other.

3. The goggle lens according to claim 1, wherein at least one of the group comprising the conductor paths and contact means is printed on.

4. The goggle lens according to claim 1, comprising a transparent, water-absorbing, internal anti-fog overcoating.

5. The goggle lens according to claim 1, comprising at least one transparent, hard layer which covers the main body at least partly.

6. The goggle lens according to claim 1, wherein the main body is curved at least partly.

7. The goggle lens according to claim 1, wherein at each side change, the respective conductor path externally runs around the main body.

8. Goggles comprising at least one goggle lens according to claim 1.

* * * * *